United States Patent
Lezdey et al.

(10) Patent No.: US 6,566,331 B1
(45) Date of Patent: May 20, 2003

(54) TREATMENT OF COLLAGEN RELATED DISEASES

(75) Inventors: Darren Lezdey, Indian Rocks Beach, FL (US); K. Anne Kronis, Tampa, FL (US); John Lezdey, Indian Rocks Beach, FL (US)

(73) Assignee: Alphamed Pharmaceutical Corp, Clearwater, FL (US)

( * ) Notice: Subject to any disclaimer, the term of this patent is extended or adjusted under 35 U.S.C. 154(b) by 171 days.

(21) Appl. No.: 09/723,840

(22) Filed: Nov. 28, 2000

Related U.S. Application Data

(63) Continuation-in-part of application No. 09/241,754, filed on Feb. 1, 1999.

(51) Int. Cl.[7] .................. A61K 38/57; A61K 38/55; A61K 38/16
(52) U.S. Cl. .................. 514/12; 514/2; 514/8
(58) Field of Search .................. 514/2, 12, 8

(56) References Cited

U.S. PATENT DOCUMENTS

| | | | | |
|---|---|---|---|---|
| 4,496,689 A | * | 1/1985 | Mitra .................. 435/174 |
| 4,877,791 A | * | 10/1989 | Sherman .................. 514/282 |
| 5,093,316 A | * | 3/1992 | Lezdey et al. .................. 514/12 |
| 5,114,917 A | * | 5/1992 | Lezdey et al. .................. 514/12 |
| 5,190,917 A | * | 3/1993 | Lezdey et al. .................. 514/12 |
| 5,215,965 A | * | 6/1993 | Lezdey et al. .................. 514/12 |
| 5,364,840 A | * | 11/1994 | Basava et al. .................. 514/12 |
| 5,492,889 A | * | 2/1996 | Lezdey et al. .................. 514/12 |
| 5,633,227 A | * | 5/1997 | Muller et al. .................. 435/226 |
| 5,780,440 A | * | 7/1998 | Lezdey et al. .................. 424/94.2 |
| 5,861,264 A | * | 1/1999 | Elrod et al. .................. 435/7.1 |
| 5,994,357 A | * | 11/1999 | Theoharides .................. 514/254.07 |
| 6,303,619 B1 | * | 10/2001 | Linden .................. 514/263.34 |

FOREIGN PATENT DOCUMENTS

| WO | WO 9734628 A1 | * | 9/1997 | .......... A61K/38/57 |

OTHER PUBLICATIONS

DeClerck et al., "Protease Inhibitors: Role and Potential Therapeutic Use in Human Cancer" (1994) Eur. J. Canc., 30A(14), 2170–2180.*

Husson et al., "Immunochemical Study on Serum Proteins in Systemic Sclerosis" (1977) Biomedicine, 26(3), 182–187, in CA: AN 1977:482303.*

Whicher et al., "The Prostaglandin–Induced Acute Phase Response is Defective in Endotoxin Tolerant Mice and in Humans with Scleroderma" (1982) Ann. N. Y. Acad. Sci., 389, 474–475.*

* cited by examiner

*Primary Examiner*—Jon P. Weber
(74) *Attorney, Agent, or Firm*—John Lezdey

(57) ABSTRACT

The present invention provides for the treatment of a patient suffering from a collagen related disease utilizing a serine protease inhibitor. The treatment includes the use of a corticosteroid that is administered separately or in combination. The serine proteases preferred are alpha 1-antitrypsin, alpha 2-macroglobulin and secretory leucocyte protease inhibitor.

10 Claims, No Drawings

TREATMENT OF COLLAGEN RELATED DISEASES

This is a Continuation-in-part of Ser. No. 09/241,754, filed Feb. 1, 1999.

FIELD OF THE INVENTION

The present invention relates to the treatment of collagen related diseases in mammals. More specifically, there is provided the treatment of interstitial cystitis, scleraderma, rheumatoid arthritis, and the like with serine protease inhibitors.

BACKGROUND OF THE INVENTION

Interstitial cystitis (IC) is characterized by a symptom complex which includes chronic, irritative and painful voiding symptoms that are associated with histological nonspecific chronic inflammation and cystoscopic finds of glomerulation and/or ulcers. It occurs primarily in women (10:1, female-to-male ratio), however, it has been diagnosed in children and adolescents. It is now believed that this clinical syndrome is multifactorial and involved several mechanisms. The hypothesized causes include infection, alternations in the glycosaminoglycan layer, lymphovascular obstruction, neurogenic disorders, endocrinologic disturbances, psychoneuroses, autoimmune disorders and nonspecific and nonspecific or immune-mediated inflammation. The disease is considered by many as being related to the collagen diseases.

Scleroderma is characterized by a thickening of the collagen. Telangrectase can appear on the face, chest, fingers and the tongue. In the gastrointestinal tract, Barrett's metaplasia of the esophagus occurs in about one third of all patients. Pneumatosis cytoides intestinalis may occur following degeneration of muscularis mucosa.

Briefly, the collagen diseases are characterized by a compaction or thickening of connective tissues which is generally treated by administration of corticosteroids alone or with immunosuppressive drugs. Inflammation is usually not present.

Many references disclose the concept of polyethylene glycol (PEG) derivatization of proteins such as alpha-1-proteinase inhibitor, asparaginase, uricase, superoxide dismutase, streptokinase, plasminogen activator, IgG, albumin, lipoprotein lipase, horseradish peroxidase, catalase, arginase and asparaginase, as well as peptides. Such derivatization through lysines was reported as improving half-life, decreasing immunogenicity, increasing solubility, and in general, increasing efficacy (which permitted less frequent dosing). In most cases, the proteins required multiple modifications per molecule to achieve improved performance in vivo, and the activity in vitro was significantly decreased by such modification.

Patents and patent publications that disclose use of polyvinyl alcohol (PVA) in protein conjugation reactions include U.S. Pat. Nos. 4,296,097 and 4,430,260, relating to conjugation of benzylpenicillin and PVA, U.S. Pat. No. 4,496,689 (EP No. 147,761), relating to conjugation of alpha-1-proteinase inhibitor with a polymer such as heparin,. PVA or PEG, EP No. 142,125 published May 22, 1985, disclosing non-covalent bonding of hemoglobin to PVA as a carrier, DE No. 2,312,615, relating to cross linked, water-insoluble PVA coupled to a protein, and DE No. 3,340,592 published May 23, 1985, relating to conjugates of PVA with human hemoglobin A, all of which are herein incorporated by reference.

Alpha$_1$-antitrypsin ($_1$-AT) belongs to serpin superfamily of serine protease inhibitor. It is a small glycoprotein which is mostly synthesized in the liver and has a molecular weight of 53,000 daltons. Human $_1$-proteinase inhibitors are involved in the regulation of proteolysis, such as the coagulation pathway, fibrinolysis, tissue destruction by endogenous serine proteinases and inflammation.

U.S. Pat. No. 5,492,889 to Lezdey et al, which is herein incorporated by reference, discloses the treatment of mast cell tumors by the administration of alpha 1-antitrypsin alone or in combination with other serine protease inhibitors.

SUMMARY OF THE INVENTION

The present invention provides a method of treating collagen related diseases including diffuse connective tissue diseases, pulmonary fibrosis, splenomegaly, interstitial cystitis, scleroderma and vasculitis.

According to one embodiment of the invention, there is provided the treatment of interstitial cystitis by the intravesical instillation of a serine protease inhibitor. More specifically, the treatment provides instilling into the bladder a composition containing an effective amount of a serine protease inhibitor selected from the group consisting of alpha 1-antitrypsin, alpha-2-macroglobulin, secretory leucocyte protease inhibitor (SLPI) and mixtures thereof, their derivative, analogs or conjugates.

Furthermore, there is provided the treatment of urinary incontinence in individuals who have interstitial cystitis or symptoms thereof.

It is a general object of the invention to provide a composition and method for treating collagen diseases.

It is a further object of the invention to provide a composition for treating individuals having the symptoms of interstitial cystitis.

It is another object of the invention to treat an incontinent individual wherein the incontinence is caused as a result of interstitial cystitis.

It is yet another object of the invention to treat scleraderma.

It is still a further object to provide a method and composition for treating rheumatoid arthritis which is characterized by compaction of collagen at the joints.

It is a still further object of the invention to treat animals which also develop collagen related diseases, especially canine and horses.

DESCRIPTION OF THE PREFERRED EMBODIMENTS

In accordance with one embodiment of the invention, there is provided a method for the treatment of individuals suffering from interstitial cystitis or symptoms thereof by the intravesical instillation of a serine protease inhibitor. The method consists of the administration an effective therapeutic amount of a protease inhibitor selected from the group consisting of alpha 1-antitrypsin, alpha 2-macroglobulin, secretory leucocyte, protease inhibitor or mixtures thereof and analogs or derivatives or conjugates thereof. The preferred conjugate is that with polyethylene glycol or an amphiphilic molecule.

Accordingly, a composition containing at least about 10 mg of protease inhibitor in a suitable pharmaceutical vehicle is instilled into the bladder.

Preferably, about 20 to 40 mg of the protease inhibitor in its natural, transgenic or recombinant form is dissolved in an aqueous medium, such as a saline or buffer solution, and instilled into the bladder. A corticosteroid may be included in the treating composition. The treatment provides immediate relief of pain since the kinins and kallikreins can be controlled together with healing of lesions or ulcers.

A cocktail of protease inhibitors is particularly effective which includes alpha 1-antichymotrypsin because it can control basophil infiltration.

Serine protease inhibitors have been found to play a major role in the direct controlling elastase activity which may also be present in arthritis. The almost immediate disappearance of pain indicates that there can be a control of the kinins as well. A cocktail of serine protease inhibitors their analogs, salts, derivatives or appears to provide the quickest healing when used in combination with a corticosteroid.

According to another embodiment of the invention, there is provided a method for topically treating skin and joints effected by compaction of collagen by use in combination with a penetrating agent such as dimelthylsulfoxide (DMSO) or insulin or some other penetrating agent which is known in the art.

The method provides the topical, oral, parental or suppository administration of a protease inhibitor selected from the group consisting of alpha 1-antitrypsin, alpha 2-macroglobulin, secretory leucocyte protease inhibitor or mixtures thereof, their derivatives.

The drug can be administered in unit dosage form containing about 10 to 20 mg per day depending on the severity of the disease. The use of controlled release substances, for example, liposomes, diketopyperazine microparticles as disclosed by U.S. Pat. Nos. 5,620,708 and 5,503,852 which are herein incorporated by reference, and the delivery systems of U.S. Pat. No. 5,620,708 which is herein incorporated by reference.

It is understood that the different components used in the treatment of the diseases can be administered in a single unit dose or separately depending upon the patient and the severity of the disease. In most cases, where the patient is a child, the use of a steroid should be avoided.

Patients with severe interstitial cystitis may also develop significant malabsorption due to increased mast call infiltrates in the lamina propria of the small intestine and perhaps secondary to circulating inflammatory mediators. In adults 40–60 mg/d of oral steroid should accompany the treatment with the protease inhibitor.

The amount of steroid utilized is generally about 0.05 to 5%, preferably, about 0.5 to 2% by weight of composition in unit dosage form.

The corticosteroids which can be used in the treatment of the diseases include triamcinolone acetonide, fluroandrenolide, prednisone, beclomethasone valerate, amcinolone, dexamethasone, betamethasone valerate, halocinonide, clocortolone and hydrocortisone valerate.

The protease inhibitor is formulated in a non-toxic, stable, pharmaceutically acceptable aqueous carrier medium, preferably at a pH of about 3 to 8, more preferably 5–8, for administration by conventional protocols and regimens, preferably systemic, including intravenous administration. For in vitro applications, as for diagnostic purposes, the modes of administration and formulation are not critical. Aqueous formulations compatible with the culture or perfusion medium will generally be used. When used in vivo for therapy, the composition may include conventional physiologically acceptable excipients, such as water for injection, buffers, and stabilizers, as is known in the art. A water-soluble carrier such as mannitol may optionally be added to the medium. A summary of formulation techniques for pharmaceutical compositions, including protein, is found, for example; in *Remington's Pharmaceutical Sciences*, Mack Publishing Co., Easton, Pa., latest edition.

The dosage level of protein in the formulation will depend on the in vivo efficacy data obtained after preclinical testing and may vary depending upon the clinical application. The medium in which the protein is dissolved will be at a pharmaceutically acceptable pH when the mixture is reconstituted.

If the formulation is lyophilized, the lyophilized mixture may be reconstituted by injecting into the vial a conventional parenteral aqueous solvent such as, e.g., distilled water for injection.

The reconstituted formulation prepared as described above is suitable for parenteral administration to humans or other mammals in therapeutically effective amounts (i.e., amounts that eliminate or reduce the patient's pathological condition without mortality or unacceptable morbidity) to provide therapy thereto.

The dose and dosage regimen of the protein will depend, for example, upon the pharmacokinetics of the drug, the nature of the disease or condition, the characteristics of the particular protein, its therapeutic index, its spectrum of activities, the patient, and the patient's medical history. Different modified proteins are expected to have different pharmacokinetic and therapeutic properties that are advantageous for different routes of administration. A long-acting drug might only be administered every 3–4days, every week, or once every two weeks.

The following examples further illustrate the practice of this invention, but are not intended to be limiting thereof. It will be appreciated that the selection of actual amounts of specific protease inhibitor to be administered to any individual patient will fall within the discretion of the attending physician and will be prescribed in a manner commensurate with the appropriate risk:benefit ratio for that particular patient. Appropriate dosages will depend on the patient's age, weight, sex, stage of disease and like factors uniquely within the purview of the attending physician.

EXAMPLE 1

A 19 patient study of women with interstitial cystitis was conducted for four weeks. Three of the patients were diagnosed as being urinary incontinent. The diagnosis of IC was considered as being mild to severe. Powdered alpha 1-antitrypsin (40 mg) was dissolved in 40 ml of saline solution. The solutions were instilled into the bladder for 20 minutes weekly for four weeks. Cystoscopy was carried out during and after filling the bladder for one minute at a pressure of 80 cm of water under spinal and general anesthesia. Bladder biopsies were carried out during cystoscopy. 24-hour collection for measurement of creatine, methylhistamine and tryptase were taken.

The weekly studies showed a decrease of creatine, methylhistamine and tryptase. After two weeks, the incontinent patients were continent and cystoscopy showed a substantial decrease in lesions. In lieu of the recombinant or natural alpha 1-antitrypsin, the conjugate with PEG may be used.

EXAMPLE 2

A composition for installation into bladders of patients having interstitial cystitis was prepared as follows:

| Ingredients | Amount |
| --- | --- |
| 2% saline solution | 40 ml |
| alpha 1-antitrypsin | 10 mg |
| triamcinolone acetonide | 0.5 mg |

The composition can be instilled weekly in the bladder of individuals having IC.

EXAMPLE 3

The drug in liposomes that can be administered orally in order to transgress the gastric barrier and prevent disintegration in the stomach is prepared as follows.

Following the procedure of U.S. Pat. No. 4,239,754, a lipid phase made up of the three components lecithin, cholesterol and dicetyl-phosphate in a molar ratio of 7:2:1 is prepared with 2.6 g of lecithin, 4.4 g of cholesterol and 0.31 g of dicetyl-phosphate by dissolving in 50 ml of chloroform and the solution was evaporated. 0.5 g of alpha 1-antitrypsin was dissolved in saline solution together with 0.1 g of betametasone and added to the phospholipids. The mixture is then subject to sonification for 10 seconds.

The composition can be used to orally treat gastrointestinal disease and to treat the symptoms thereof. In lieu of alpha 1-antitrypsin, there can be used alpha 2-macroglobulin.

EXAMPLE 4

A salve comprising 1% alpha 1-antitrypsin was prepared with Aquaphor® and 1% water. The salve was used daily on a patient having scleroderma of the finger. The finger was bent and constricted. The skin around the finger was hardened. After a daily application for one month the skin was softer, the finger was more flexible and the bending was less severe.

After the treatment was stopped, the finger within six months returned to the bent position.

EXAMPLE 5

A 5 percent solution of alpha 1-antitrypsin was prepared with DMSO. A patient with rheumatoid arthritis administered the composition to an arthritic knee. After one week of treatment, the knee was free of pain, had greater flexibility and a substantial reduction in swelling.

What is claimed is:

1. A method for treating mammals suffering from a collagen related disease selected from the group consisting of interstitial cystitis, scleroderma, and rheumatoid arthritis which comprises administering an effective amount of a composition comprising a protease inhibitor selected form the group consisting of alpha 1-antitrypsin and secretory leucocyte protease inhibitor and mixtures in a suitable pharmaceutical carrier.

2. The method of claim 1 further comprises administering a corticosteroid.

3. The method of claim 1 wherein the disease is interstitial cystitis and an aqueous composition is instilled into the bladder.

4. The method of claim 1 wherein the disease is scleroderma.

5. The method of claim 4 wherein said composition comprises alpha 1-antitrypsin in a solution comprising dimethyl sulfoxide that is administered topically.

6. The method of claim 5 further comprises administering a corticosteroid.

7. The method of claim 1 wherein said disease is rheumatoid arthritis.

8. The method of claim 7 wherein the disease is treated topically with said composition at the site of said disease.

9. The method of claim 7 wherein the disease is treated by injection of said composition to the site of the disease.

10. A method for treating mammals suffering from interstitial cystitis by instilling into the bladder an effective amount of an aqueous composition of alpha1-antitrypsin or alpha1-antitrypsin conjugated to polyethylene glycol.

* * * * *